(12) United States Patent
Teetzel

(10) Patent No.: US 10,688,325 B2
(45) Date of Patent: Jun. 23, 2020

(54) EYE-PROTECTIVE SHIELD WITH HEAD UP DISPLAY

(71) Applicant: WILCOX INDUSTRIES CORP., Newington, NH (US)

(72) Inventor: James W. Teetzel, Portsmouth, NH (US)

(73) Assignee: Wilcox Industries Corp., Newington, NH (US)

( * ) Notice: Subject to any disclaimer, the term of this patent is extended or adjusted under 35 U.S.C. 154(b) by 921 days.

(21) Appl. No.: 14/600,810

(22) Filed: Jan. 20, 2015

(65) Prior Publication Data

US 2015/0217145 A1    Aug. 6, 2015

Related U.S. Application Data

(60) Provisional application No. 61/936,082, filed on Feb. 5, 2014.

(51) Int. Cl.
| | |
|---|---|
| *A62B 18/00* | (2006.01) |
| *A62B 18/08* | (2006.01) |
| *A61F 9/04* | (2006.01) |
| *A62B 18/02* | (2006.01) |
| *G02B 27/01* | (2006.01) |
| *G02B 5/22* | (2006.01) |
| *A62B 9/00* | (2006.01) |

(52) U.S. Cl.
CPC ............ *A62B 18/082* (2013.01); *A61F 9/045* (2013.01); *A62B 9/006* (2013.01); *A62B 18/02* (2013.01); *A62B 18/08* (2013.01); *G02B 5/22* (2013.01); *G02B 27/0101* (2013.01); *G02B 27/0149* (2013.01); *G02B 27/0189* (2013.01); *G02B 2027/019* (2013.01); *G02B 2027/0141* (2013.01)

(58) Field of Classification Search
CPC ....... A62B 18/082; A62B 18/08; A62B 9/006; A62B 18/02; G02B 27/0149; G02B 27/0189; G02B 27/0101; G02B 5/22; G02B 2027/0141; G02B 2027/019; A61F 9/045
See application file for complete search history.

(56) References Cited

U.S. PATENT DOCUMENTS

| | | | | |
|---|---|---|---|---|
| 4,352,353 A * | 10/1982 | Bolton | ................... | B64D 10/00 128/201.24 |
| 6,442,767 B1 * | 9/2002 | Meckes | .................... | A42B 3/22 2/10 |
| 6,720,878 B2 * | 4/2004 | Jumpertz | ............. | A42B 3/0433 340/286.05 |

(Continued)

*Primary Examiner* — Steven O Douglas
(74) *Attorney, Agent, or Firm* — McLane Middleton, Professional Association

(57) ABSTRACT

In one aspect, an eye shield for a respirator mask of the type having a face piece adapted to fit over the face of a user is provided. The eye shield includes a visor assembly including a visor surrounded by a frame, the visor assembly configured to be removably mounted in an opening in the face piece. One or more fastener elements are provided on the frame for removably securing the visor assembly to the face piece. The visor is formed of a transparent material which filters electromagnetic energy emissions at one or more preselected wavelengths. In certain embodiments, one or more head up display assemblies are attached to the visor assembly for projecting a human viewable image to the visor.

19 Claims, 6 Drawing Sheets

(56) References Cited

U.S. PATENT DOCUMENTS

| | | | | |
|---|---|---|---|---|
| 6,826,783 | B1* | 12/2004 | Grove | A42B 3/10 |
| | | | | 128/201.25 |
| 8,082,922 | B2* | 12/2011 | McWilliams | G02B 27/017 |
| | | | | 128/201.23 |
| 8,316,850 | B2* | 11/2012 | Grilliot | A62B 9/006 |
| | | | | 128/201.25 |
| 9,108,073 | B2* | 8/2015 | Leuschner | A62B 9/006 |
| 2005/0001728 | A1* | 1/2005 | Appelt | G08B 21/02 |
| | | | | 340/573.1 |
| 2005/0263155 | A1* | 12/2005 | Gossweiler | A62B 9/006 |
| | | | | 128/205.23 |
| 2007/0000031 | A1* | 1/2007 | Makris | A42B 3/0433 |
| | | | | 2/411 |
| 2008/0035145 | A1* | 2/2008 | Adams | A62B 18/08 |
| | | | | 128/204.18 |
| 2008/0276933 | A1* | 11/2008 | Dampney | A42B 3/28 |
| | | | | 128/201.25 |

* cited by examiner

EYE-PROTECTIVE SHIELD WITH HEAD UP DISPLAY

CROSS REFERENCE TO RELATED APPLICATION

This application claims the benefit of U.S. provisional application No. 61/936,082 filed Feb. 5, 2014, which is incorporated herein by reference in its entirety.

BACKGROUND

This invention relates to an eye shield for use with a respirator mask. In certain embodiments, an eye-protective shield is provided which includes an integrated head up display.

Respirator masks or gas masks are devices commonly used by military personnel, firefighters, and industrial workers in hazardous environments for protection from inhalation of harmful substances including smoke, chemicals, and biological agents. Such respirator masks may employ a filtration system to purify air before it is inhaled by a wearer. Alternatively, respirator masks may employ a breathing hose for delivering a breathing gas from a source of breathing gas, such as a powered air purifying system (PAPR) of a self-contained breathing apparatus (SCBA).

Military systems, such as range finding/target acquisition systems, target designator systems, illumination systems, laser direct fire simulators, and so forth. Such systems often employ lasers that output electromagnetic energy emissions at wavelengths, powers and/or intensities that can be damaging to the human eye, e.g., the retina or cornea. It would be desirable to provide a lens that would filter or attenuate laser light emitted by such military systems to prevent eye damage or blinding from occurring during training exercises or other operational use involving such military systems or otherwise render such emissions less dangerous for the eyes.

Thus, an eye-protective shield for use with a respirator mask with a laser filtering or attenuating lens to be used by an individual wearing a respirator mask is provided. In certain embodiments, the eye-protective shield herein also incorporates a head up display.

SUMMARY

In one aspect, an eye shield for a respirator mask of the type having a face piece adapted to fit over the face of a user is provided. The eye shield includes a visor assembly including a visor surrounded by a frame, the visor assembly configured to be removably mounted in an opening in the face piece. One or more fastener elements are provided on the frame for removably securing the visor assembly to the face piece. The visor os formed of a transparent material which filters electromagnetic energy emissions at one or more preselected wavelengths. In certain embodiments, one or more head up display (HUD) assemblies project information or indicia in human viewable form onto the visor.

In a further aspect, a kit is provided comprising a plurality of eye shields interchangeably attachable to the face piece of a respirator mask. The plurality of eye shields includes at least a first eye shield and a second eye shield. The first eye shield includes a first visor assembly including a first visor surrounded by a first frame. The first visor assembly is configured to be removably mounted in an opening in the face piece. A first set of one or more fastener elements is provided on the first frame for removably securing the first visor assembly to the face piece. The first visor is formed of a transparent material which filters electromagnetic energy emissions at a first wavelength. The second eye shield includes a second visor assembly including a second visor surrounded by a second frame. The second visor assembly is configured to be removably mounted in the opening in the face piece. A second set of one or more fastener elements is provided on the second frame for removably securing the second visor assembly to the face piece. The second visor is formed of a transparent material which filters electromagnetic energy emissions at a second wavelength.

In yet another aspect, a breathing apparatus comprises a face piece adapted to fit over the face of a user and an eye shield including a visor assembly. The visor assembly includes a visor surrounded by a frame and is configured to be removably mounted in an opening in the face piece. One or more fastener elements are provided on the frame for removably securing the visor assembly to the face piece. The visor is formed of a transparent material which filters electromagnetic energy emissions at one or more preselected wavelengths.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DESCRIPTION OF THE PREFERRED EMBODIMENTS

Figure 1:
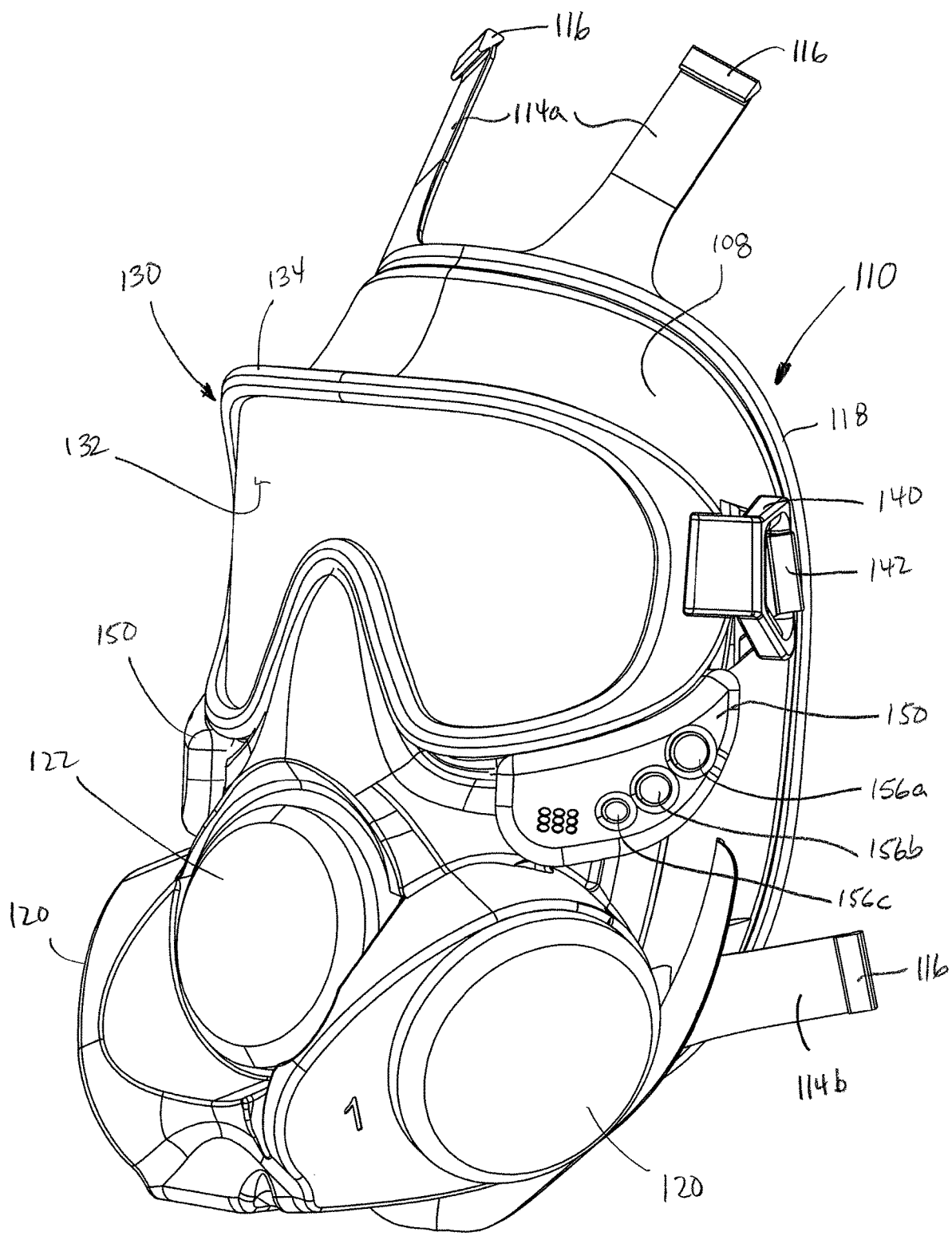
FIG. 1 is a perspective view of an eye protective shield for respirator mask according to an exemplary embodiment of the invention.
Figure 2:
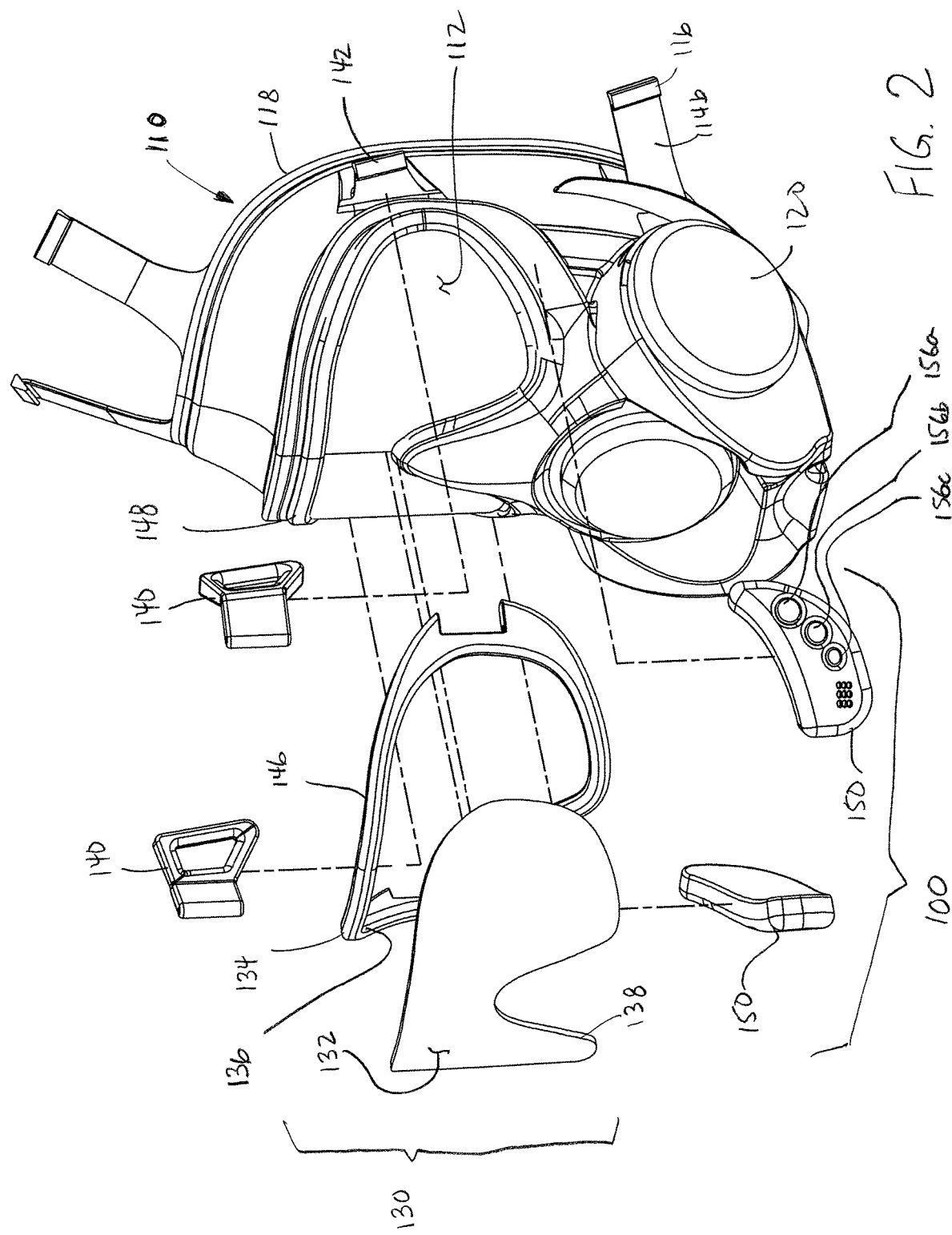
FIG. 2 is an exploded view of the shield appearing in FIG. 1.
Figure 3:
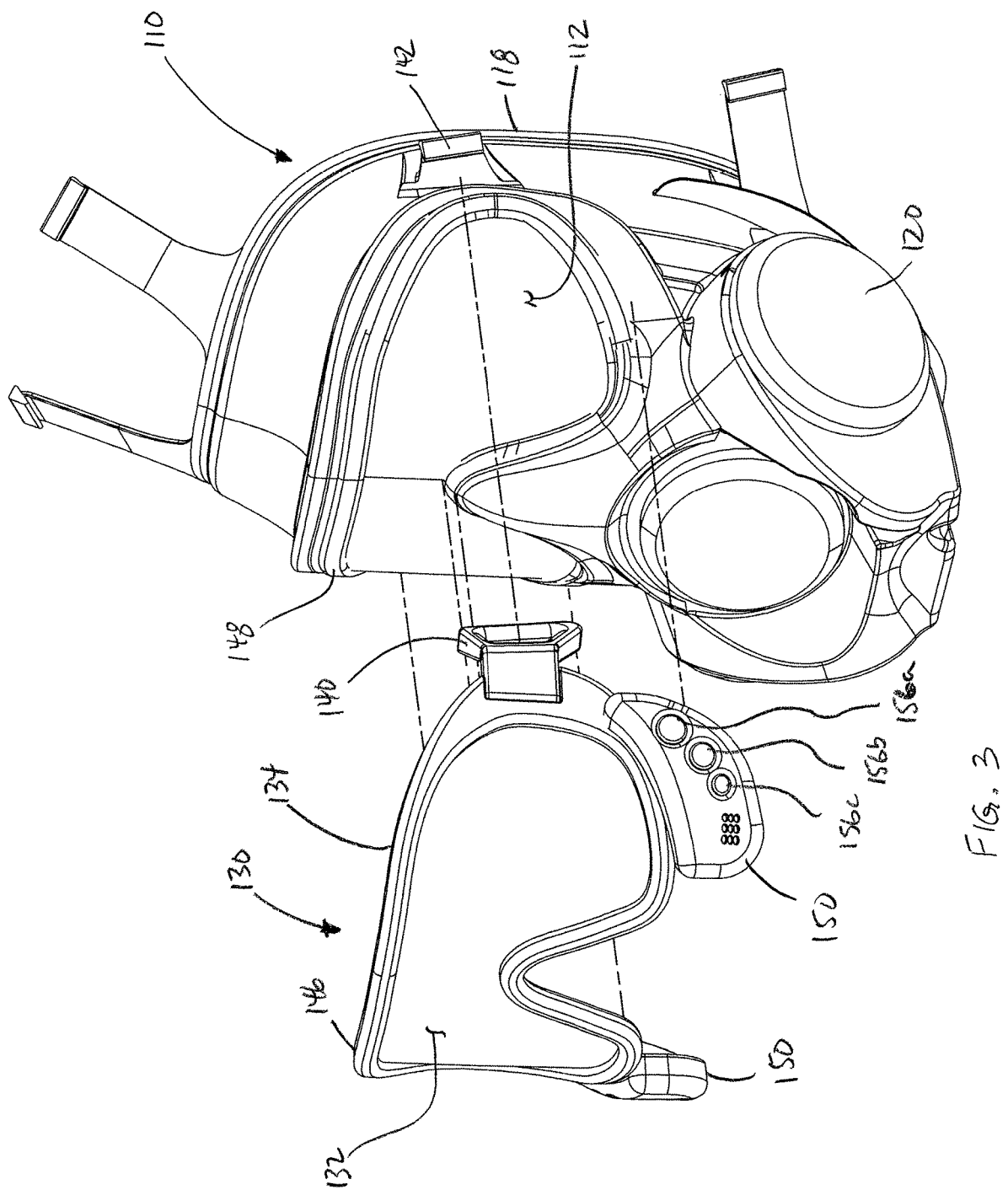
FIG. 3 illustrates the manner of attachment of the visor and HUD assembly to the face piece.

Referring now to the drawings, an eye shield assembly 100 includes a visor assembly 130 that is adapted to fit over a respirator or gas mask 110 that is worn by the user. The respirator 110 may be a commercially available respirator. In a preferred embodiment, the eye shield assembly 100 is configured to be worn over a First Responder Respirator (FRR) available from Scott Safety of Monroe, N.C. It will be recognized that the eye shield assembly 100 can be modified to accommodate alternative respirator models.

The respirator 110 includes a face piece portion 108 which may include a visor or lens 112 covering an opening in the face piece 108. The visor 112 is typically transparent non-filtering and does not offer eye protection against laser emissions. The respirator 110 is of a type in which the face piece 108 is attachable to a head worn harness or other suitable headgear via a plurality of straps 114a and 114b, which includes fasteners 116. The fasteners 116 are adapted to attach to a respective aligned strap or webbing (not shown) of a head harness assembly to secure the respirator 100 over the face of the user as would be known to persons skilled in the art.

A face seal 118 may be provided about the periphery of the face piece to prevent entry of contaminants. The respirator 110 further includes one or more fasteners 120 for attaching air purifying elements such as filtration canisters, PAPR or SCBA breathing hose, and so forth. The respirator also includes an exhalation valve 122, speech diaphragm, and so forth, as would be known to those skilled in the art.

The visor assembly 130 includes a generally transparent, eye-protective visor 132. The visor 132 is received within a frame 134. The frame 134 includes a groove or channel 136 receiving the peripheral edge 138 of the visor 132. First and second fastener elements 140 are disposed on opposite transverse sides of the frame 134 and are removably attached to complementary, aligned fastener elements 142 on the respirator 110. The frame 134 may include a peripheral edge 146 that provides a sealing engagement with the edge 148 securing the opening receiving the lens 112 of the respirator 110 to prevent entry of contaminants into the space between the lens 112 of the respirator and the visor 132.

The visor 132 is formed of a material which filters or attenuates laser or light emissions at one or more preselected wavelengths while transmitting a significant portion of visible light outside of the preselected wavelength(s), and preferably as much visible light as possible. The one or more preselected wavelengths should correspond to the wavelength(s) of emissions of a laser source or system against which the user's eyes are to be protected. The visor assembly 130 is removable from the respirator 110 and in certain embodiments can be interchanged with other visor assemblies that filter at other wavelengths, e.g., corresponding to a particular laser device or system.

Left and right head up display (HUD) assemblies 150 are attached to the frame 134 and project a human viewable image, such as information, text, indicia, images, and so forth onto the visor 132. The HUD may employ an image source or generator and associated driver electronics 152, including one or more light emitting elements, such as a liquid crystal display (LCD), light emitting diode (LED) display, spatial light modulator, or the like. Projection optics 154, which may include one or more refractive, reflective, or diffractive optical elements, for projecting the image, text, information, indicia, etc., output by the light source onto the visor 132. The images produced by the HUD assemblies are reflected off the visor 132 toward the user's eyes. In this manner, the images, information, indicia, etc., can be provided to the user without requiring the user to look away from his or her current line or sight, i.e., as would be required to view a non-HUD display, equipment display panel, or the like.

The HUD assemblies 150 each include one or more buttons or like controls 156a, 156b, and 156c, which are manually actuatable when the face shield assembly 100 is being worn. In a preferred embodiment, the button 156a may comprise an on/off button for toggling the HUD display between the powered on and powered off states. In the preferred embodiment, the button 156b may comprise a scroll button for scrolling through multiple screens or selectable menu items. The button 156c may comprise a select button allowing the user to select a given screen or menu item. In this manner, various screens, display features, configuration options, and the like can be provided via a menu driven hierarchy displayed on the visor 132 using the HUD assembly 150 and navigated using the buttons 156b and 156c.

Figure 4:
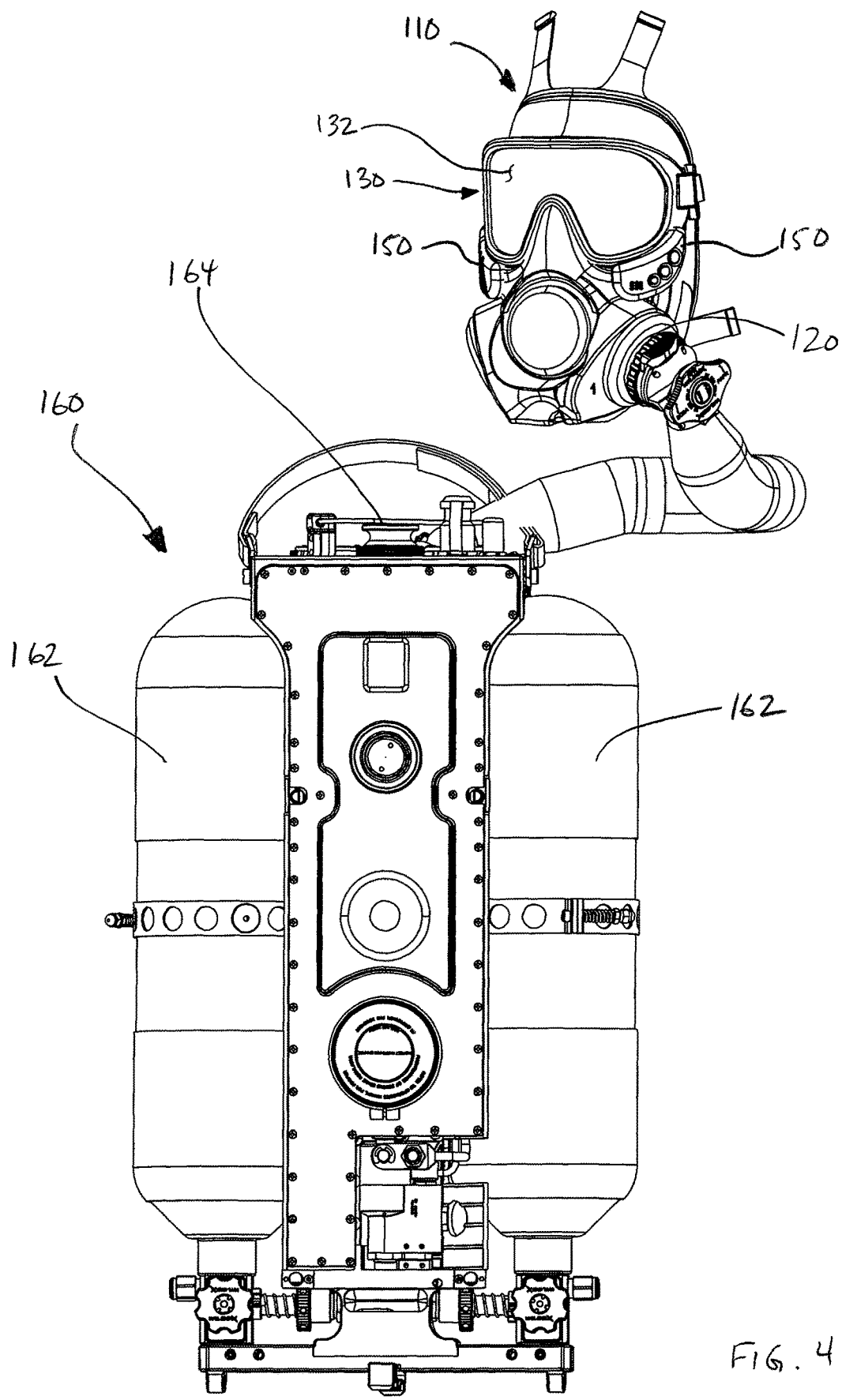
FIG. 4 illustrates the eye protective shield herein in conjunction with an SCBA and respirator.
Figure 5:
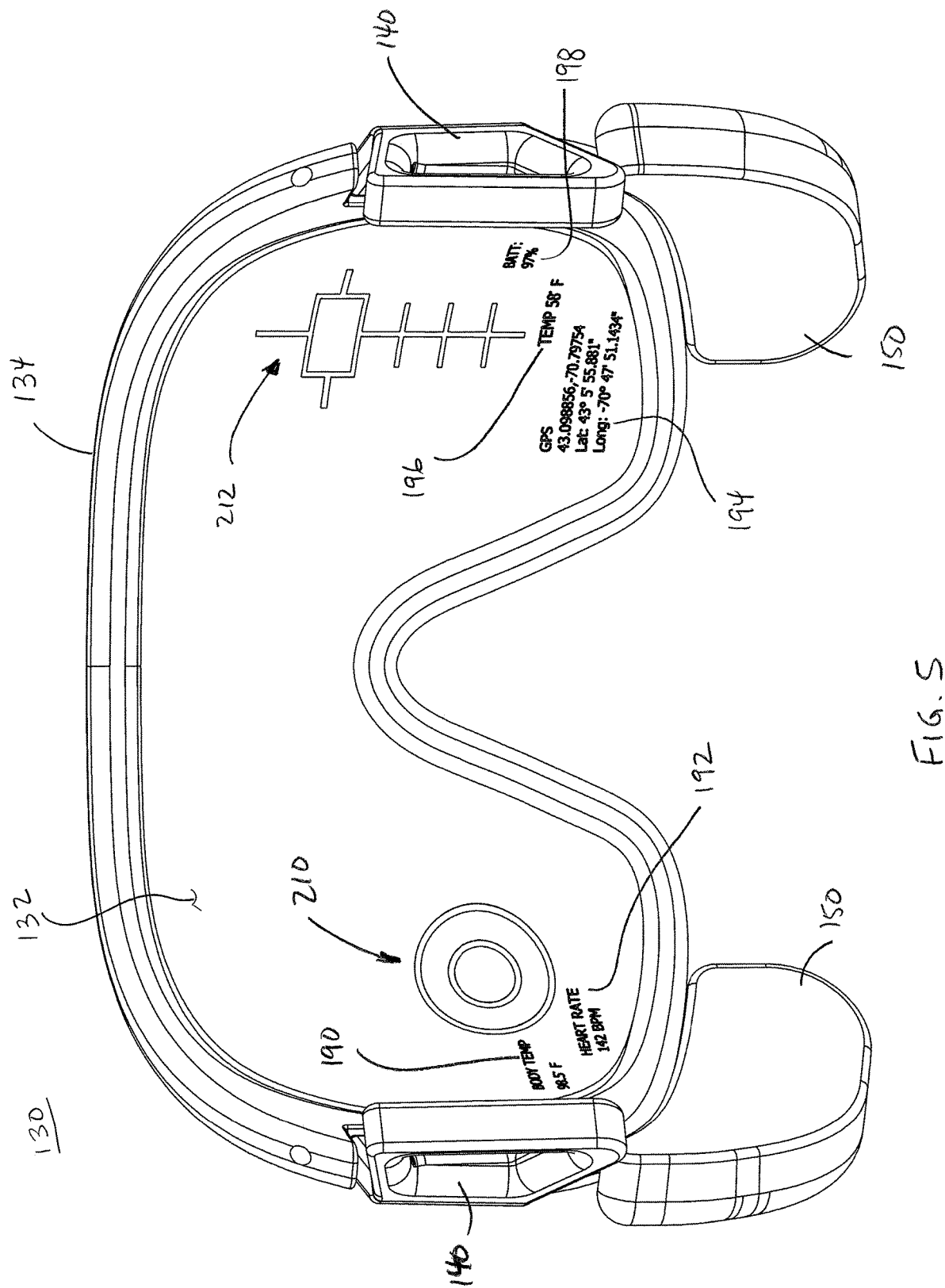
FIG. 5 illustrates the visor with exemplary HUD output from the perspective of the wearer.

Referring now to FIGS. 4 and 5 and with continued reference to FIGS. 1-3, FIG. 4 depicts an exemplary embodiment wherein the face shield assembly 100 is shown in use with a life support system 160. The life support system 160 may be a hybrid breathing system which is selectively operable in a self-contained breathing system (SCBA) mode in which breathable air/gas is provided by a self-contained air supply 162 such one or more air tanks or cylinders, and a powered air-purifying respirator (PAPR) mode of operation, in which filtered ambient air is drawn with blower assistance through one or more air filters or purifiers 164 and delivered to the user, and a non-powered air-purifying respirator (APR) mode of operation, in which in which the air is drawn through the air purifying filter(s) or canister (s) via the user's negative inhalation pressure. The life support system 160 may be as described in commonly owned U.S. Pat. No. 7,647,927, which is incorporated herein by reference in its entirety.

The life support system 160 may include one or more sensors. In exemplary embodiments, the life support system includes a vital sign monitoring system 170 for sensing one or more vital signs or health conditions of the wearer, such as heart rate, body temperature, respiratory rate, and so forth. A low battery detection circuit 172 may be provided, e.g., a circuit for monitoring the voltage level of a power supply which provides electrical power for operation of the life support system 160. An air pressure sensor 174 may be provided to sense the pressure level present in the tanks 162. A SCBA/PAPR mode readout sensor 176, such as a switch position indicator or the like, is provided to determine the current operating mode of the life support system 160.

Figure 6:
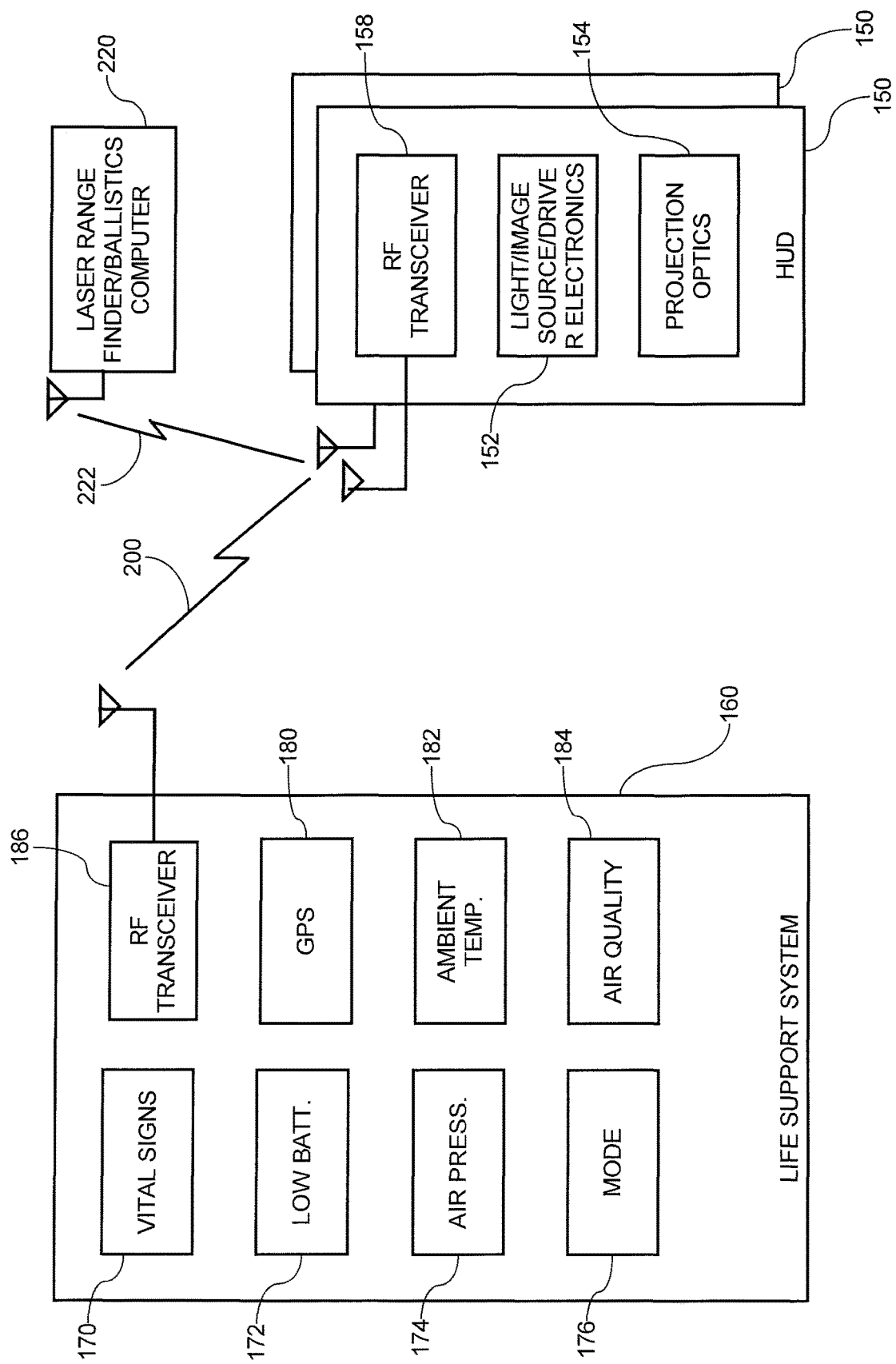
FIG. 6 is a schematic diagram of the system appearing in FIG. 4.

Other sensors contemplated include a GPS receiver 180 for determining positional information of the user and a thermometer 182 for sensing ambient air temperature. An air quality monitor 184 may be provided that samples the ambient air to detect toxic or unfilterable constituents in the ambient environment. A schematic diagram of the system appearing in FIG. 4 appears in FIG. 6. Although the sensors 170, 172, 174, 176, 180, 182, and 184 are illustrated as being integral with or associated with the life support system 160, it will be recognized that one or more of the sensors, such as the GPS receiver, ambient temperature sensor, air quality monitor, vital signs monitor, etc., may be separate from the life support system 160.

The HUD assembly 150 includes an RF transceiver, which communicates with an RF transceiver 186 in the life support system 160. The life support system 160 communicates with one or both of the HUD assemblies 150 via a wireless protocol 200, such as Bluetooth, WiFi, ZigBee, or other RF protocol.

FIG. 5 depicts a visor assembly 130 with exemplary display indicia output by the HUD assemblies 150 appearing on the visor 132, shown from the perspective of the wearer. The display indicia include body temperature indicia 190 and heart rate indicia 192, e.g., output to the HUD assemblies by the vital sign monitoring system 170. The display indicia in the depicted illustration also include GPS coordinate indicia 194, e.g., output to the HUD assembly 150 by the GPS receiver 180, ambient air temperature indicia 196, e.g., output by the thermometer 182, battery life indicia 198, e.g., representative of battery life of the power supply of the associated life support system 160.

The display indicia may further include one or more reticles, such as a first reticle 210 comprising a plurality of concentric circles or a second reticle 212, comprising a cross hair or ballistic type reticle. The reticles 210 and/or 212 may be displayed in a fixed position on the visor 132, or alternatively, one or both of the reticles 210, 212 may be displayed at a movable position on the visor 132 relative to the user's eye based on target range (e.g., ballistic drop due to gravity) and optionally other ballistics factors (e.g., temperature, wind speed and direction, elevation difference, and so forth). The target range and/or ballistics computation may be performed by a range finder unit 220 having a ballistics computer function. The range finder unit 220 is in wireless communication with one or both of the HUD assemblies 150, which outputs a display signal 222 in accordance with a Bluetooth or other wireless protocol to the HUD 150. The display signal 222 is representative of a human viewable image output to the visor to provide a visual indication of an aiming trajectory which will cause the path of a projectile fired from the user's location to intersect with the ranged target.

The invention has been described with reference to the preferred embodiment. Modifications and alterations will occur to others upon a reading and understanding of the preceding detailed description. It is intended that the invention be construed as including all such modifications and alterations insofar as they come within the scope of the appended claims or the equivalents thereof.

What is claimed is:

1. An eye shield for a respirator mask of the type having a face piece adapted to fit over the face of a user, the eye shield comprising:
   a visor assembly including a visor surrounded by a frame, the visor assembly configured to be removably mounted in an opening in the face piece;
   a sealing surface disposed on the frame which sealingly engages a surface on the face piece when the eye shield is attached to the face piece;
   one or more fastener elements on the frame for removably securing the visor assembly to the face piece;
   the visor formed of a transparent material which filters electromagnetic energy emissions at one or more preselected wavelengths; and
   at least one head up display assembly attached to the visor assembly and disposed on an exterior facing side of the eyeshield for projecting a human viewable image to the visor, wherein the at least one head up display assembly includes one or more manually actuable input devices disposed on a housing of the at least one head up display assembly, the one or more manually actuable input devices for controlling operation of the at least one head up display assembly.

2. The eye shield of claim 1, wherein the visor assembly is disposed over a transparent lens covering the opening in the face piece.

3. The eye shield of claim 1, wherein the one or more wavelengths correspond to a wavelength of a military laser system.

4. The eye shield of claim 1, wherein each of the at least one head up display assembly includes an image source for generating an image and projection optics for projecting the image onto the visor.

5. The eye shield of claim 4, wherein the image is generated responsive to image data received from an associated life support system.

6. The eye shield of claim 5, wherein the image comprises indicia selected from the group consisting of one or more of vital signs of the wearer, a geographical location of the wearer, ambient air temperature, a battery level of a power supply in the life support system, ambient air quality, targeting cross hairs, a reticle, and any combination thereof.

7. The eye shield of claim 1, wherein the at least one head up display assembly further includes an RF transceiver for receiving a signal representative of an image to be displayed.

8. The eye shield of claim 1, wherein the one or more manually actuable input devices are accessible by a user wearing the eye shield.

9. The eye shield of claim 1, wherein the one or more manually actuable input devices include one or more buttons.

10. A kit comprising a plurality of eye shields interchangeably attachable to and detachable from a respirator mask, the respirator mask having a face piece adapted to fit over the face of a user, the plurality of eye shields comprising:
    at least a first eye shield and a second eye shield;
    the first eye shield including a first visor assembly including a first visor surrounded by a first frame, the first visor assembly configured to be removably mounted in an opening in the face piece, a first set of one or more fastener elements on the first frame for removably securing the first visor assembly to the face piece, the first visor formed of a transparent material which filters electromagnetic energy emissions at a first wavelength;
    the second eye shield including a second visor assembly including a second visor surrounded by a second frame, the second visor assembly configured to be removably mounted in the opening in the face piece, a second set of one or more fastener elements on the second frame for removably securing the second visor assembly to the face piece, and the second visor formed of a transparent material which filters electromagnetic energy emissions at a second wavelength; and
    at least one head up display assembly attached to one or both of the first visor assembly and the second visor assembly, the at least one head up display assembly disposed on an exterior facing side of the eyeshield, the at least one head up display assembly for projecting a human viewable image to a respective one of the first visor and second visor, wherein the at least one head up display assembly includes one or more manually actuable input devices disposed on a housing of the at least one head up display assembly, the one or more manually actuable input devices for controlling operation of the at least one head up display assembly.

11. The kit of claim 10, further comprising the respirator mask.

12. A breathing apparatus, comprising:
    a face piece adapted to fit over the face of a user;
    an eye shield including a visor assembly, the visor assembly having a visor surrounded by a frame, the visor assembly configured to be removably mounted in an opening in the face piece;
    a sealing surface disposed on the frame which sealingly engages a surface on the face piece when the eye shield is attached to the face piece;
    one or more fastener elements on the frame removably securing the visor assembly to the face piece;
    the visor formed of a transparent material which filters electromagnetic energy emissions at one or more preselected wavelengths; and
    at least one head up display assembly attached to the visor assembly and disposed on an exterior facing side of the eyeshield for projecting a human viewable image to the visor, wherein the at least one head up display assembly includes one or more manually actuable input devices disposed on a housing of the at least one head up display assembly, the one or more manually actuable input devices for controlling operation of the at least one head up display assembly.

13. The breathing apparatus of claim 12, further comprising:
one or more fasteners for attaching an air purifying element.

14. The breathing apparatus of claim 12, further comprising a life support apparatus.

15. The breathing apparatus of claim 12, wherein the life support apparatus is selected from the group consisting of a self-contained breathing system, an air purifying respirator, and a combined self-contained breathing system and an air purifying respirator.

16. The breathing apparatus of claim 12, wherein the one or more manually actuable input devices are accessible by a user wearing the eye shield.

17. The breathing apparatus of claim 16, wherein the one or more manually actuable input devices include one or more buttons.

18. The kit of claim 10, wherein the one or more manually actuable input devices are accessible by a user wearing the eye shield.

19. The kit of claim 18, wherein the one or more manually actuable input devices include one or more buttons.

\* \* \* \* \*